United States Patent
Ohkawa

[19]

[11] Patent Number: 6,027,623
[45] Date of Patent: Feb. 22, 2000

[54] DEVICE AND METHOD FOR ELECTROPHORETIC FRACTION

[75] Inventor: Tihiro Ohkawa, La Jolla, Calif.

[73] Assignee: Toyo Technologies, Inc., La Jolla, Calif.

[21] Appl. No.: 09/064,798

[22] Filed: Apr. 22, 1998

[51] Int. Cl.[7] .......................... G01N 27/26; G01N 27/447
[52] U.S. Cl. ............................................ 204/450; 204/600
[58] Field of Search .................................... 204/600, 601, 204/602, 603, 604, 605, 606, 450, 451, 452, 453, 454, 455, 456; 422/101; 436/161, 177

[56] References Cited

U.S. PATENT DOCUMENTS

| | | |
|---|---|---|
| 4,683,202 | 7/1987 | Mullis . |
| 4,811,218 | 3/1989 | Hunkapiller et al. . |
| 4,965,188 | 10/1990 | Mullis et al. . |
| 5,038,852 | 8/1991 | Johnson et al. . |
| 5,121,320 | 6/1992 | Aoki et al. . |
| 5,427,663 | 6/1995 | Austin et al. . |
| 5,637,458 | 6/1997 | Frankel et al. ............................... 435/6 |
| 5,837,115 | 11/1998 | Austin et al. ............................ 204/450 |

*Primary Examiner*—Jill Warden
*Assistant Examiner*—John S. Starsiak, Jr.
*Attorney, Agent, or Firm*—Nydegger & Associates

[57] ABSTRACT

A device for fractionating macromolecules in a fluid medium includes a plurality of individual obstacles which are arranged on a substrate in rows and columns. An electric field is provided and oriented to move the macromolecules in migration through fluid channels that are established between the columns of obstacles. Each obstacle has mutually symmetrical right and left front walls which are inclined to a respective fluid channel. Consequently, as macromolecules diffuse through the fluid medium from a fluid channel during their migration through the device, the front walls of the obstacles redirect them back into the same fluid channel from which they diffused. As a result, the faster diffusing, smaller macromolecules take longer to migrate through the fluid channels of the device. Eventually, because the diffusion rate of the macromolecules depends on their size, the positions of the macromolecules in the device reflect their respective diffusion rates, and therefore their size.

17 Claims, 3 Drawing Sheets

DEVICE AND METHOD FOR ELECTROPHORETIC FRACTION

FIELD OF THE INVENTION

The present invention pertains generally to measuring instruments. More particularly, the present invention pertains to a device for fractionating macromolecules in a fluid medium. The present invention is particularly, but not exclusively, useful for fractionating macromolecules with a mechanical sieve having a high throughput.

BACKGROUND OF THE INVENTION

The characterization and fractionation of macromolecules, such as DNA and protein, are among the most important diagnostic techniques used in biotechnology today. Heretofore, the most widely used method for fractionation of macromolecules has been a process known as gel electrophoresis.

In a gel electrophoresis process, the macromolecules are forced to migrate through the pores of the gel under the influence of a driving force. Normally, this driving force is a uniform electric field (E), and the velocity of the macromolecules through the gel is dependent on the electric field. The actual direction of macromolecule movement through the electric field (E) will be determined by the charge on the molecule which, depending on the nature of the molecule, may be either positive or negative. It happens that DNA in a fluid medium, such as water, will have a negative charge. It also happens that the speed (i.e. the magnitude of the velocity) at which the macromolecules migrate through the gel is dependent on physical characteristics of the macromolecule. In the case of DNA, it is the length of the various macromolecules which determines their respective speed of migration through the gel. Consequently, after a period of time, a gel electrophoresis process will fractionate the DNA macromolecules according to their length.

Recently, there have been several attempts to perform electrophoresis using micro-sieves rather than gels. Specifically, micro-sieves have been manufactured for this purpose using the well known techniques and processes which were originally developed for the fabrication of integrated circuits (IC) on silicon wafers. In the manufacture of a micro-sieve a pattern of obstacles, rather than circuits, is fabricated on the wafer surface by photolithography and plasma assisted etching. For a micro-sieve, the resultant pattern of obstacles acts much like an obstacle course, or sieve, which impedes the migration of macromolecules across the wafer surface. It happens that the arrangement of the obstacles on the wafer surface, as well as the structural configuration of the obstacles, together determine the operational efficacy of the particular micro-sieve. Several examples can be given.

U.S. Pat. No. 5,427,663 which issued to Austin et al. for an invention entitled "Microlithographic Array for Macromolecule and Cell Fractionation" provides an example wherein a micro-sieve is produced with an array of obstacles which may be of various shapes such as round posts, rectangular bunkers, or v-shaped or cup-shaped structures. According to the disclosure of Austin et al., fractionation of macromolecules and cells is accomplished by impeding the movement of the macromolecules and cells through the micro-sieve. Thus, for the method to work, it is apparent that the size of the obstacles must be comparable to the size of the macromolecules. Macromolecules which are effectively smaller that the spacing between obstacles will be unaffected by the micro-sieve and, therefore, not fractionated.

The importance of being able to fractionate macromolecules which are smaller than the obstacles in a micro-sieve is underscored by the limitations that are imposed by current IC fabrication techniques. At present, the highest resolution for mass produced IC chips using photolithography is approximately 0.25 micron. With electron lithography, this resolution can be improved to approximately 0.1 micron. Electron lithography, however, is a much slower process than photolithography and, in any event, DNA macromolecules are often less than 0.1 micron in length.

To address the obstacle/macromolecule size discrepancy, T. A. J. Duke and R. H. Austin [Phys. Rev. Let. 80 pp. 1552,1998], and D. Ertas [Phys. Rev. Let. 80 pp. 1548, 1998] have independently proposed a method for electrophoresis in which macromolecules are fractionated according to their propensity to diffuse due to the Brownian Motion experienced during their migration through a fluid medium. Specifically, it is known that smaller (i.e. shorter) macromolecules will diffuse more rapidly in a fluid medium than will larger (i.e. longer) macromolecules. Relying on this phenomenon, Duke, Austin, and Ertas have proposed a micro-sieve with obstacles that are asymmetric left and right, relative to the direction of macromolecule migration through the micro-sieve. Due to this asymmetry, the obstacles guide the diffused macromolecules in a lateral direction, and thereby cause the macromolecules to fan out. More specifically, as the macromolecules fan out, they become fractionated according to their propensity to diffuse. For DNA molecules this fractionation results in a separation according to length. Importantly, with a micro-sieve having asymmetric obstacles, macromolecules which are smaller than the spacings between the obstacles can be fractionated. The major disadvantage of this method, however, is that the macromolecules must be injected into the micro-sieve within a very small area (essentially a point source) in order to maintain effective resolution. This results in a very low throughput.

In light of the above, it is an object of the present invention to provide a device with a micro-sieve for fractionating macromolecules in a fluid medium (and its method of use) which is able to fractionate macromolecules that are smaller in size than the spacings between obstacles in the micro-sieve. It is another object of the present invention to provide a device for fractionating macromolecules which has the capacity for a high throughput of macromolecules. Still another object of the present invention is to provide a device for fractionating DNA macromolecules according to the lengths of the DNA macromolecules. Yet another object of the present invention is to provide a device with a micro-sieve for fractionating macromolecules which can sequentially rerun macromolecules through the micro-sieve to improve resolution of the fractionated macromolecules. Another object of the present invention is to provide a device for fractionating macromolecules which is relatively easy to manufacture, is simple to use, and is comparatively cost effective.

SUMMARY OF THE PREFERRED EMBODIMENTS

In accordance with the present invention, a device for fractionating macromolecules in a fluid medium includes a substrate with a planar surface which is formed with a plurality of obstacles. The obstacles extend outwardly from the planar surface, and more specifically, the obstacles are arranged on the substrate's planar surface in a matrix of columns and rows. Within this arrangement, the columns of obstacles establish a plurality of substantially parallel fluid channels which are each bounded by a pair of columns of obstacles. Similarly, the rows of obstacles establish a plurality of substantially parallel fluid passageways which are perpendicular to the fluid channels. Each fluid passageway is bounded by a pair of rows of obstacles.

A voltage source is provided, and connected to the device in order to establish a substantially uniform electric field (E) over the planar surface of the substrate. Specifically, the electric field is oriented substantially parallel to the plurality of fluid channels. For purposes to be disclosed below in conjunction with the operation of the device of the present invention, the electric field can be varied both in its magnitude, and in its direction on the substrate.

It is an important aspect of the present invention that the obstacles be symmetrically configured and properly oriented on the substrate's planar surface. Specifically, each obstacle is formed with a left front wall and a right front wall which are symmetrical to each other as they face generally into the direction of the electric field. Further, both of the front walls are inclined from a normal to the longitudinal axes of the fluid channels at an angle $\alpha_1$. Similarly, each obstacle is formed with a left rear wall and a right rear wall. These rear walls, like the front walls, are also symmetrical to each other. They, however, are inclined from the normal to the longitudinal axes of the fluid channels at an angle $\alpha_2$. Preferably, the angle $\alpha_2$ is greater than the angle $\alpha_1$.

In the operation of the device of the present invention, a buffer solution (fluid medium) containing the DNA macromolecules to be fractionated is introduced into the device along one edge of the substrate. This is similar to gel electrophoresis. As the DNA macromolecules enter the device they become subject to the influence of the electric field and begin to migrate through the fluid channels. Importantly, in order for the substrate and obstacles not to disturb the electric field, the substrate and obstacles are made of a material which is permeable to the buffer solution, such as a porous silicon.

As the macromolecules migrate through the fluid channels of the micro-sieve, it happens that the macromolecules diffuse through the buffer solution at rates which are inversely related to their size, i.e. smaller macromolecules diffuse faster. As between migration and diffusion, by far the most dominant macromolecular movement is in the direction of migration established by the electric field. Nevertheless, the tendency for diffusion is sufficiently great so that as the macromolecules leave an opening between obstacles on opposite sides of the fluid channel, not all will pass through the next downstream opening. Instead, at least some of the macromolecules (the smaller ones) will diffuse into the fluid passageway between rows of obstacles to a point where they will miss the next opening in the fluid channel.

When a macromolecule misses an opening, it will be intercepted by an obstacle. The intercepted macromolecule, still under the influence of the electric field, is then redirected along the inclined front wall of the obstacle. Importantly, the intercepted macromolecule is redirected back into the same fluid channel from which it diffused. Meanwhile, the larger macromolecules in the fluid medium, which have diffused more slowly, proceed through the opening unaffected.

As the process is continued, the larger, slower diffusing macromolecules will pass through more openings in the fluid channel before being diffused out of the fluid channel to be intercepted by an obstacle. Thus, the larger macromolecules proceed through the fluid channels at a faster rate than do the smaller, but faster diffusing macromolecules. Indeed, the larger the macromolecule, the faster that macromolecule will proceed through a fluid channel. Eventually, after a period of time the positions of the macromolecules in the fluid channel reflect their diffusion rate and, therefore, the size of the molecules.

Obviously, the longer the fluid channels can be, the better will be the resolution that is achieved between the sizes of the DNA macromolecules. Long fluid channels, however, are not necessarily the most cost effective configuration for the device of the present invention. It happens that by periodically reversing the electrical field, it is possible to cause a reverse migration that is sufficiently rapid to minimize diffusion of the macromolecules through the device. The initial electric field can then be subsequently reestablished after each reversal and the length of the fluid channels can thereby be effectively lengthened. As intended for the present invention, several reversals in the direction of the electrical field are possible.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
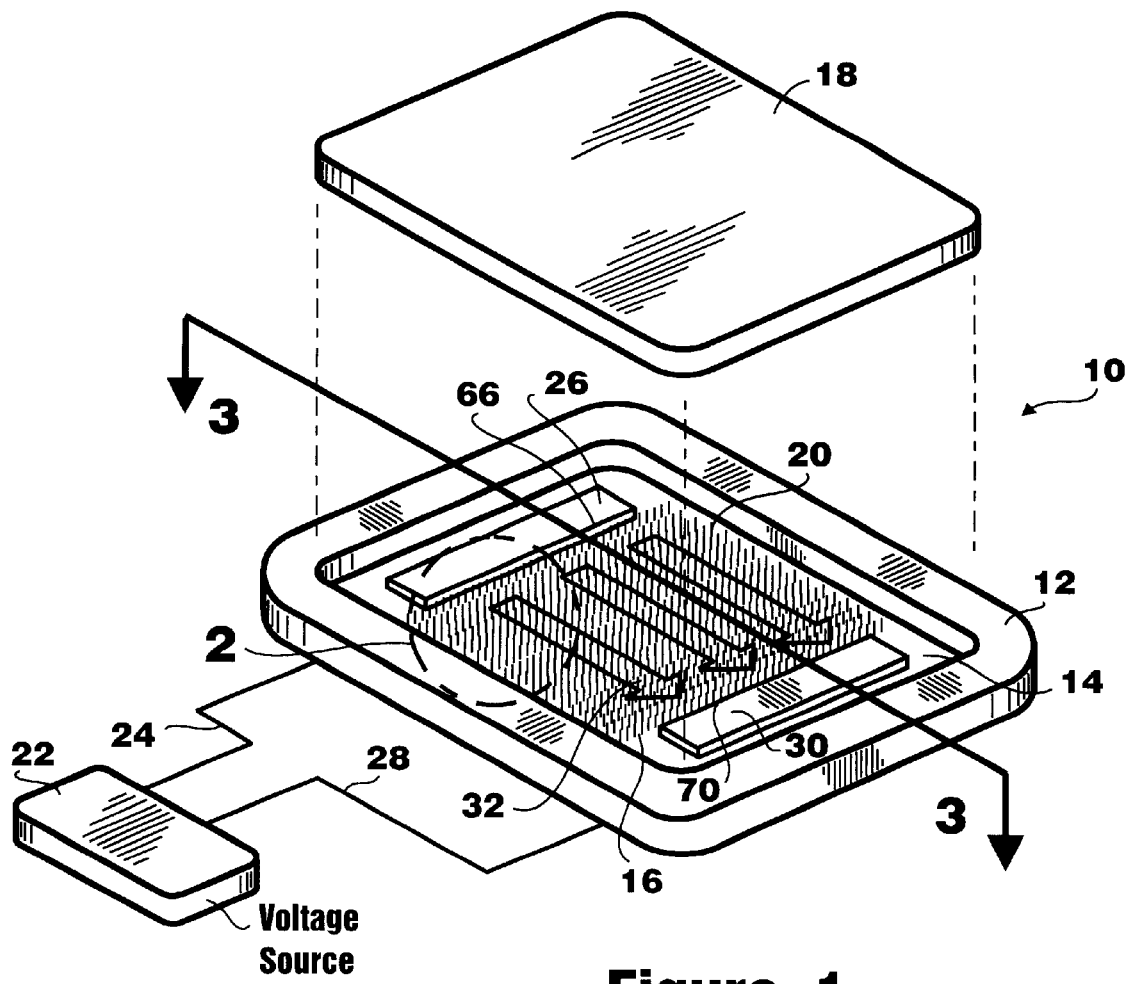
FIG. 1 is a perspective view of the fractionation device of the present invention.

Referring initially to FIG. 1, a device for fractionating macromolecules in a fluid medium is shown and generally designated 10. As shown, the device 10 includes a receptacle 12 which is formed with a depression 14. Also, as indicated in FIG. 1, a substrate 16 can be positioned in the depression 14 to act as a floor of the depression 14. A lid 18 is provided which covers the depression 14 to enclose a micro-sieve 20 between the lid 18 and the substrate 16. Importantly, the lid 18 must fit tightly onto the receptacle 12 so that a fluid medium will be confined for movement only through the micro-sieve 20. For the purposes of the present invention, it is to be appreciated that the micro-sieve 20 can be fabricated or formed on Substrate 16 using well known techniques for the manufacture of integrated circuit (IC) chips. Specifically, the micro-sieve 20 can be fabricated on substrate 16 by such methods as photolithography and plasma assisted etching.

FIG. 1 also shows that the device 10 includes a voltage source 22 which has an electrical lead 24 that is connected to an electrode 26. The electrode 26 is located in the depression 14 substantially as shown. Additionally, the voltage source 22 has an electrical lead 28 which is connected to an electrode 30. Like electrode 26, the electrode 30 is located in the depression 14. Importantly, the electrode 26 is positioned in the depression 14 opposite the electrode 30 with the micro-sieve 20 therebetween. With this configuration, an activation of the voltage source 22 can establish a substantially uniform electric field E through the micro-sieve 20 substantially as indicated by the arrows 32. It is to be appreciated that, as contemplated by the present invention, electrode 26 can be either a cathode or an anode with electrode 30 being, respectively, an anode or a cathode. Accordingly, the direction of the electric field E can be reversed. Further, purposes of the present invention, the strength of the uniform electric field E can be somewhat less than about one hundred volts per centimeter (E≦100V/cm). Due to the fact that operation of the device 10 will require the depression 14 be filled with a fluid medium which covers the substrate 16 and micro-sieve 20, the materials to be used for substrate 16 and micro-sieve 20 are an important concern. Preferably, in order for the substrate 16 and micro-sieve 20 to not interfere with the electric field E that is generated by the voltage source 22 while the device 10 is filled with a fluid medium, the substrate 16 and micro-sieve 20 should be made of a material such as a porous silicon.

Figure 2:
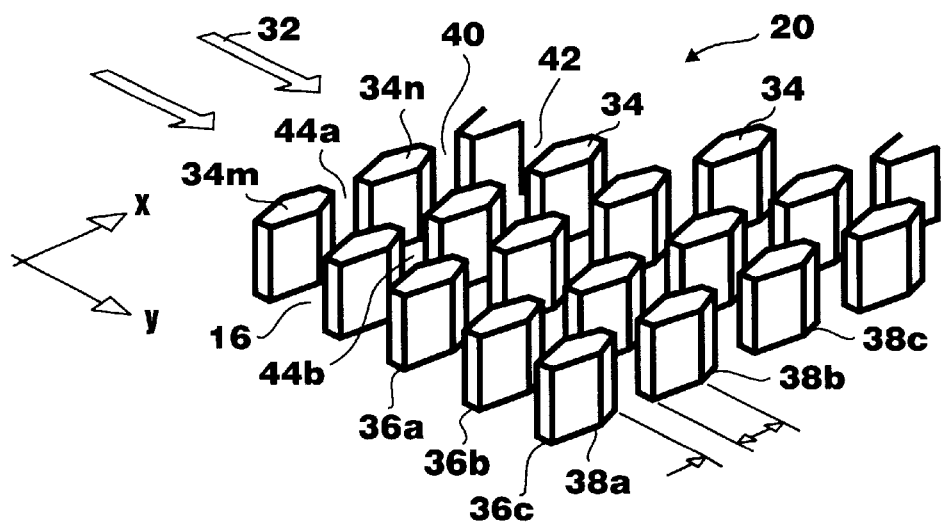
FIG. 2 is an enlarged view of the sieve used for the present invention seen within the area encircled by the line 2—2 in FIG. 1.

FIG. 2 indicates that the micro-sieve 20 comprises a plurality of obstacles 34. Specifically, the plurality of obstacles 34 are formed to extend outwardly and away from the substrate 16. Also, as shown, the obstacles 34 are arranged as a matrix on the substrate 16. This matrix includes a plurality of rows 36, which extend in the x direction (rows 36a–c are exemplary), and a plurality of columns 38, which extend in the y direction (columns 38a–c are also exemplary). The obstacles 34 then create a plurality of substantially parallel fluid channels 40 which are aligned in the y direction, with each fluid channel 40 being bounded by a pair of columns 38. Also, the obstacles 34 create a plurality of substantially parallel fluid passageways 42 which are oriented perpendicular to the fluid channels 40 and which are aligned in the x direction. Each fluid channel 42 is thus bounded by a pair of rows 36. FIG. 2 further shows that in each of the fluid channels 40, an opening 44 is established between adjacent obstacles 34 on opposite sides of the fluid channels 40. By way of example, the obstacles 34m and 34n shown in FIG. 2 establish the opening 44a.

Figure 3:
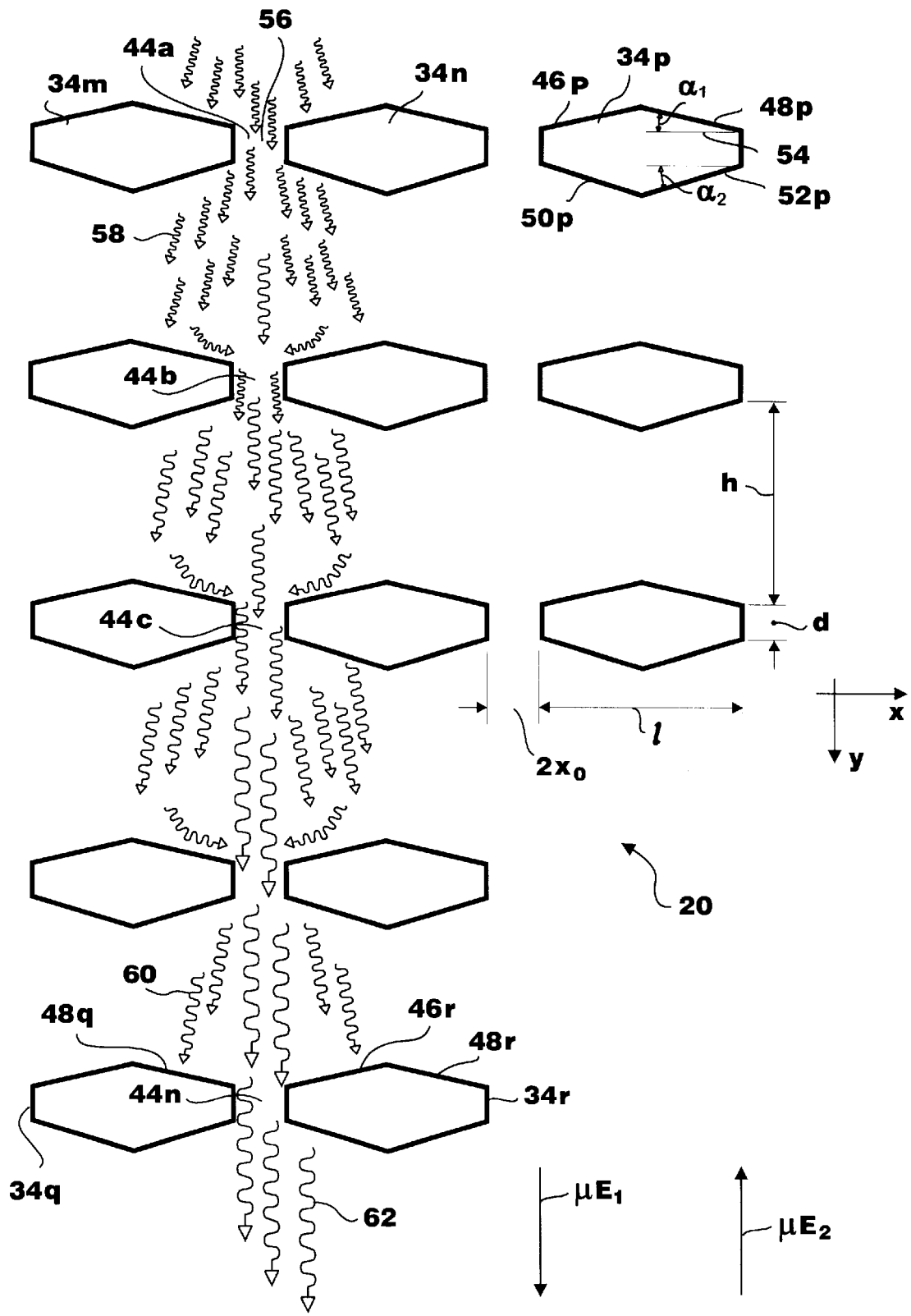
FIG. 3 is a top plan view of obstacles in the sieve arranged in rows and columns, and showing the passage of macromolecules between a pair of columns as seen from the perspective of line 3—3 in FIG. 1.

The structural configuration for each obstacle 34 is perhaps best appreciated by cross referencing FIGS. 2 and 3. By way of example, consider the obstacle 34p (shown in FIG. 3). For orientation purposes, the x and y directions will be taken to be as shown in the Figures. Accordingly, the uniform electric field E may be oriented in either the ±y directions (see arrows 32 for +y direction). Further, it is to be understood that the front of an obstacle 34 actually faces in the negative y direction. Consequently, the rear of an obstacle 34 faces in the positive y direction. The right side of the obstacle 34 then faces in the positive x direction while the left side of the obstacle 34 faces in the negative x direction. With this in mind, it will be seen that the obstacle 34p includes a left front wall 46p and a right front wall 48p. Further the obstacle 34p includes a left rear wall 50p and a right rear wall 52p.

As shown in FIG. 3, the left front wall 46p of obstacle 34p is symmetrical with its right front wall 48p. Specifically, this symmetry is established relative to a plane (not shown) which is perpendicular to the x axis and which passes through the obstacle 34p to separate the left front wall 46p from the right front wall 48p. Further, it will be appreciated that the symmetrical walls 46p and 48p are both inclined at an angle $\alpha_1$ from a line 54 which is parallel to the x axis and, thus, perpendicular to the plane. For purposes of the present invention, the angle $\alpha_1$ is preferably less than about forty five degrees ($\alpha_1 < 45°$). Using a similar geometrical description, it will be easily appreciated that the left rear wall 50p and the right rear wall 52p of obstacle 34p are also symmetrical with respect to each other. They are also inclined. The rear walls 50p and 52p are, however, inclined at an angle $\alpha_2$ which, preferably, is greater than the angle $\alpha_1$ (i.e. $\alpha_2 > \alpha_1$).

OPERATION

The operation of the device 10 of the present invention relies on the fact that the movement of macromolecules through the micro-sieve 20 is essentially a random process which involves diffusion of the macromolecules through a fluid medium. This diffusion is in addition to the normal mobility of the macromolecules in the fluid medium. The two can be individually analyzed. In the absence of diffusion, all macromolecules, regardless of their size, will travel under the influence of an electrical field E at the same velocity. This velocity (v) can be expressed in terms of the macromolecular mobility ($\mu$) and the electric field (E) as:

$$v = \mu E$$

In the absence of diffusion, the trajectories of all macromolecules would be straight lines. Diffusion, however, introduces a randomness that needs to be accounted for and, as indicated above, is relied upon by the present invention for resolution of the macromolecules in fractionation.

Since diffusion is a random process, the movement of a macromolecule should be described probabilistically. For this purpose, consider a macromolecule beginning its journey through the micro-sieve 20 as it exits from the middle of opening 44a at a start point 56. The probability P[x,y] of finding the molecule at x=x after it has traveled from start point 56 to y=y is given by:

$$P[x,y]dx = [v/\{4\pi D y\}]^{1/2} \exp[-x^2 v/\{4 D y\}] dx$$

where, $v = \mu E$ as indicated above, and where D is the diffusion coefficient for the particular macromolecule. It is known that the value of D is dependent upon physical characteristics of the macromolecule, such as size or length.

Figure 4:
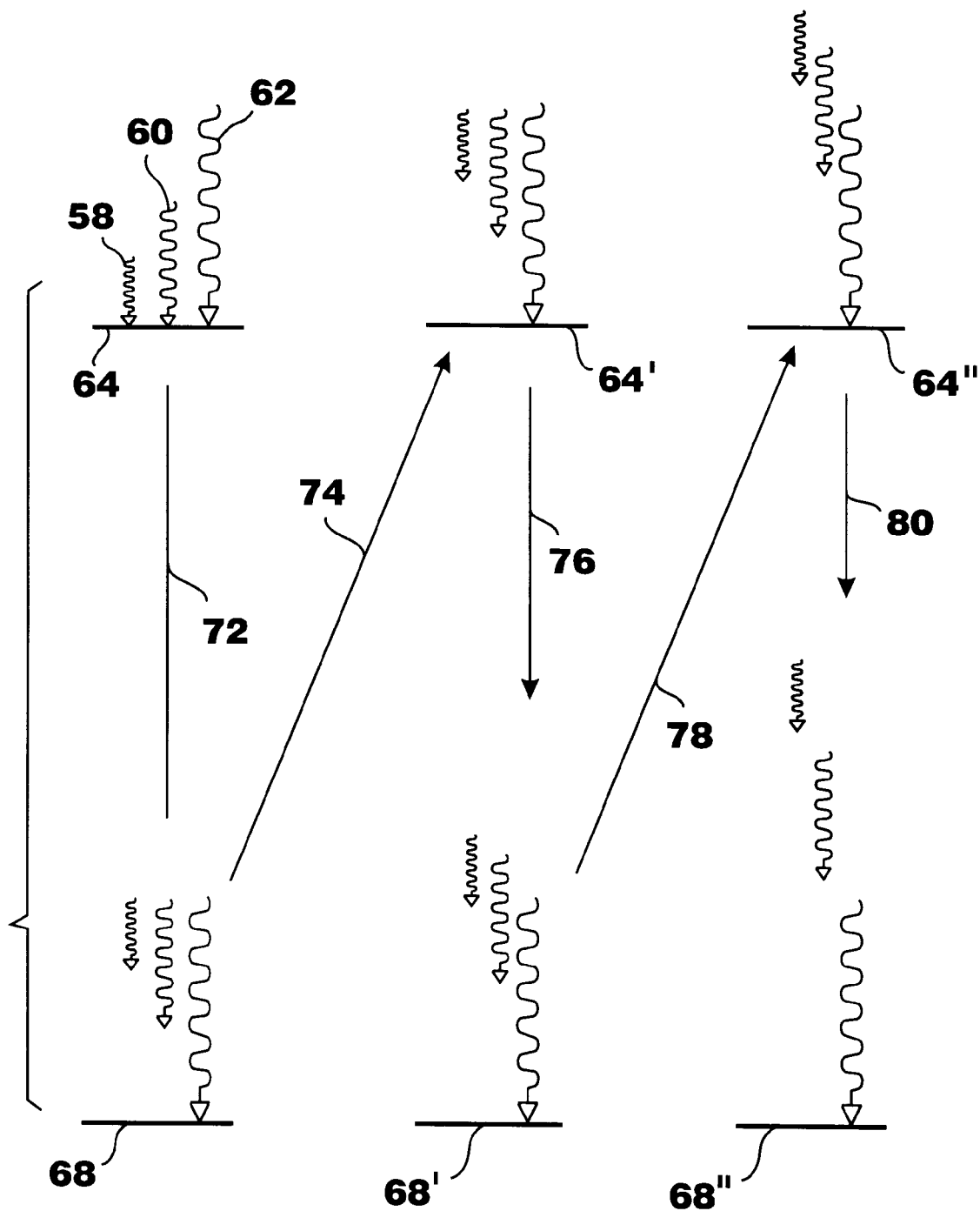
FIG. 4 is a graphical sequence depicting the relative speed of migration of different macromolecules through the sieve in response to changes in the direction of the electric field.

For the purposes of this disclosure, FIGS. 3 and 4 show three different sized DNA macromolecules. Specifically, these are a short macromolecule 58, a medium sized macromolecule 60, and a long macromolecule 62. Accordingly, due to their size, each of the macromolecules (58, 60, 62) will have a different diffusion coefficient, D. It thereby happens that the short macromolecules 58 have the greatest propensity to diffuse while the long macromolecule 62 have the least. There are, of course, various gradations therebetween (e.g. macromolecule 60). Further, while the disclosure herein has thus far referred only to macromolecules (58, 60, 62), it is to be appreciated that the device and methods of the present invention are equally capable of processing many other type individual microstructures, such as free cells, viruses, or minute particles. In any event, depending on its size, and other physical characteristics, each microstructure will have its own diffusion coefficient D.

Referring again to FIG. 3, by using geometric relationships it can be shown that as a macromolecule exits an opening 44 at a point $x_0$, and diffuses from a straight path down the fluid channel 40, it will be intercepted by the next downstream obstacle 34 at a point where:

$$y = h - d - [x - x_0] \tan \alpha$$

In this expression, h is the distance between obstacles 34 in the y direction, and d is the depth of the obstacle 34 as shown in FIG. 3. Also, it can be shown that the time, $\tau_1$, for the macromolecule to move along a front wall 48 of the obstacle 34 and come back to an opening 44, after being intercepted by the obstacle 34, is given by the expression:

$$\tau_1 = [x - x_0]/[\mu E \sin \alpha \cos \alpha]$$

Due to the fact that, absent an interception by an obstacle 34, each macromolecule will travel at the same speed through the fluid medium in micro-sieve 20 (recall, $v = \mu E$), it is apparent that when a macromolecule does collide with an obstacle 34 it will linger to some extent. Therefore, its transit time through the micro-sieve 20 will be lengthened. With this in mind, it can be shown mathematically that the average time, $<\tau>$, for a macromolecule to pass from one row 36 to another (i.e. from one opening 44 to the next downstream opening 44) can be given by the expression:

$$<\tau> = h[1+\beta]/[\mu E]$$

wherein:

$$\beta = [4D/\pi v\ h]^{1/2}/\sin \alpha.$$

Further, because each macromolecule 58, 60, 62 will diffuse differently, the difference in the respective transit times, $\delta<\tau>$, between macromolecules having a difference in diffusion coefficient, $\delta D$, is given by the expression:

$$\delta<\tau>/<\tau> = \beta[1+\beta]^{-1}\delta D/[2D]$$

The consequence of the above is that it takes the short macromolecules 58 the longest period of time to progress through the micro-sieve 20, while the long macromolecules 62 will progress therethrough in the shortest time interval. Stated differently, the fractionation of macromolecules is possible because of the significant differences between their diffusion rates. However, because diffusion is a random process, the randomness of macromoleculer migration must also be accounted for. It happens that after passing N rows 36, of the device 10, macromolecules having the same diffusion coefficient, D, will experience a relative spread in the y direction, due to randomness, which can be expressed as $N^{-\frac{1}{2}}$. Therefore, effective resolution requires that the differences in macromolecular migration speed due to different coefficients of diffusion be larger, or more pronounced, than the spread caused by randomness.

From the above comparisons it is obvious that the more rows 36 there are in the micro-sieve 20, and therefore the more openings 44 through which the macromolecules 58, 60, 62 must pass, the better will be the resolution obtained when fractionating macromolecules 58, 60, 62. In fact, for N number of rows 36, it can be shown that the resolution of separation of macromolecules is given by the expression:

$$\delta D/D = 2N^{-1/2}\ (1+\beta)/\beta$$

As indicated above, the length of each DNA macromolecule is a determining characteristic in the fractionation process. Accordingly, where M is the number of base pairs for a particular DNA, the length resolution can be given by the expression:

$$\delta M/M = 4N^{-1/2}\ (1+\beta)/\beta$$

It should also be noted that, since the pairs of columns 38 which bound each of the fluid channels 40, will effectively and independently fractionate all of the macromolecules 58, 60, 62 which pass through that particular fluid channel 40, the throughput for device 20 can be increased merely by adding additional fluid channels 40. There are, of course, practical limits to both the number of rows 36 and the number of columns 38 which can be fabricated for the device 10.

For an example of an operational process, as contemplated for the present invention, consider the micro-sieve 20 to be a square of 4 cm×4 cm, with 8000×8000 obstacles 34 on edge. DNA fragments having an M equal to 100 will have the mobility ($\mu$) of $2.5 \times 10^{-8}$ m$^2$ sec$^{-1}$ V$^{-1}$ and a diffusion coefficient (D) of $1.4 \times 10^{-11}$ m$^2$ sec$^{-1}$. For an applied voltage of 80 volts from voltage source 22, the macromolecules will travel the length of the micro-sieve 20 in approximately eighteen minutes. During this migration, the dispersion $\delta D/D$ will be about 3% and the length resolution $\delta M/M$ will be about 6%. These numbers, or course, are only representative.

As indicated above, it is within the contemplation of the present invention that, in order to improve resolution of the macromolecules 58, 60, 62, they can be forced to make several migrations through the micro-sieve 20. An illustrative example of what happens to the macromolecules 58, 60, 62 during a sequence of repeated migrations through the micro-sieve 20 is provided by FIG. 4.

The macromolecules 58, 06, 62, shown at position 64 in FIG. 4, are considered to be randomly mixed. Such a random mix is most likely when the macromolecules in a fluid medium are first introduced into the device 10 at the edge 70 of micro-sieve 20. Due to this randomness, they will all start their migration through the micro-sieve 20 together from the position 64. Under the influence of the uniform electric field $E_1$ (see FIG. 3), the macromolecules 58, 60, 62 will then migrate through the micro-sieve 20, in a manner disclosed above with reference to FIG. 3. This migration continues, until they arrive at a position 68 which is preferably near the edge 70 of micro-sieve 20. In FIG. 4, this initial migration of the macromolecules 58, 60, 62 is represented by the arrow 72.

Note that by the time the macromolecules 58, 60, 62 arrive at the position 68, they have started to fractionate. It may be that one such trip is sufficient for the particular purposes. On the other hand, additional fractionation may be desired. If so, a reverse electric field $E_2$ (again see FIG. 3) may be imposed on the micro-sieve 20 to influence a reverse migration of the macromolecules 58, 60, 62. During this reverse migration (represented by the arrow 74 in FIG. 4), the macromolecules 58, 60, 62 will be returned from the position 68 to a position 64' which is approximately the same as the initial start position 64. An objective during this reverse migration through the micro-sieve 20 is to leave previous fractionation of macromolecules 58, 60, 62 effectively undisturbed. To do this, a combination of factors can be manipulated. Preferably, the angle $\alpha_2$ for rear walls 50,52, is chosen so that the obstacles 34 will not unnecessarily impede the reverse migration of diffused macromolecules 58, 60, 62. Further, the magnitude of the reverse electric field $E_2$ should be sufficiently greater than the magnitude of the electric field $E_1$, and be applied for a sufficiently shorter period time so that diffusion is minimized during the reverse migration. Once the macromolecules 58, 60, 62 have been returned to position 64', the electric field $E_1$ can again be applied to influence the macromolecules 58, 60, 62 for normal migration again through the micro-sieve 20 toward the position 68' (arrow 76). As many additional migrations (arrow 78) and subsequent reverse migration (arrow 80) can be made as desired. As indicated by the macromolecules 58, 60, 62 at positions 68' and 68", with each migration, enhanced resolution in the fractionation of the macromolecules 58, 60, 62 is possible.

While the particular device and method for electrophoretic fractionation as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for fractionating macromolecules in a fluid medium which comprises:

a substrate having a substantially planar surface;

a voltage source for creating a substantially uniform electric field, said electric field being oriented on said substrate to move the macromolecules in a direction of migration over said planar surface; and a plurality of individual obstacles extending outwardly from said planar surface and arranged in a plurality of rows and a plurality of columns to establish a plurality of fluid channels with each said fluid channel being bounded by a pair of said columns of obstacles, and wherein each said obstacle has a left front wall and a right front wall, said front walls being symmetrical to each other and respectively inclined to redirect macromolecules diffused from one said fluid channel back into said same fluid channel during migration of the macromolecules through said device, wherein each said obstacle further includes a left rear wall and a right rear wall, said rear walls being symmetrical to each other and respectively inclined to redirect macromolecules diffused from one said fluid channel back into said same fluid channel during a reverse migration of the macromolecules through said device, wherein said front walls of said obstacles are inclined from a normal to the direction of migration at an angle $\alpha_1$ and said rear walls are inclined thereto at an angle $\alpha_2$, wherein the angle $\alpha_1$ is less than approximately forty five degrees ($\alpha_1 < 45°$) and wherein $\alpha_2$ is greater than $\alpha_1$ ($\alpha_2 > \alpha_1$).

2. A device as recited in claim 1 wherein said substrate is a porous silicon.

3. A device as recited in claim 1 wherein said substrate has a first end and a second end with opposite edges therebetween, and wherein the macromolecules are injected into said device at said first end for migration through said device toward said second end.

4. A device as recited in claim 1 wherein said front walls of said obstacles are flat.

5. A device as recited in claim 1 wherein said uniform electric field is less than approximately one hundred volts per centimeter.

6. A device as recited in claim 1 wherein the number of columns is equal to the number of rows.

7. A device for fractionating large and small macromolecules according to the diffusion rates of their respective sizes which comprises:

a substrate formed with a plurality of substantially parallel fluid channels, each said fluid channel having a first side, and a second side opposite said first side;

a voltage source for creating a substantially uniform electric field, said electric field being directed substantially parallel to said fluid channels to define a longitudinal first direction of migration for the macromolecules through said fluid channels;

a plurality of walls erected along each of said first and second sides of said respective fluid channels, with each said wall being inclined to said direction of migration to redirect macromolecules diffused from one of said fluid channels back into said same fluid channel during migration of the macromolecules through said device; and a means for periodically reversing said uniform electric field to define a second direction of migration, the magnitude of said uniform electric field being greater in the second direction than in the first direction said second direction being substantially opposite said first direction to allow more time for said faster diffusing small macromolecules to leave said channel and separate from said large macromolecules.

8. A device as recited in claim 7 wherein each said wall is formed on an individual obstacle.

9. A device as recited in claim 8 wherein said individual obstacles are arranged in M number of columns and N number of rows to establish an M×N matrix with each said fluid channel being bounded by a pair of said columns of said obstacles.

10. A device as recited in claim 9 wherein each said obstacle is formed with a left front wall and a right front wall, said front walls being symmetrical to each other and respectively inclined to redirect macromolecules diffused from one said fluid channel back into said same fluid channel during migration of the macromolecules through said device.

11. A device as recited in claim 10 wherein each said obstacle further includes a left rear wall and a right rear wall, said rear walls being symmetrical to each other and respectively inclined to redirect macromolecules diffused from one said fluid channel back into said same fluid channel during a reverse migration of the macromolecules through said device.

12. A device as recited in claim 11 wherein said front walls of said obstacles are inclined from a normal to the direction of migration at an angle $\alpha_1$ and said rear walls are inclined thereto at an angle $\alpha_2$.

13. A device as recited in claim 12 wherein the angle $\alpha_1$ is less than approximately forty five degrees ($\alpha_1 < 45°$) and wherein $\alpha_2$ is greater than $\alpha_1$ ($\alpha_2 > \alpha_1$).

14. A device as recited in claim 7 wherein said substrate is a porous silicon.

15. A device as recited in claim 7 wherein said uniform electric field is less than approximately one hundred volts per centimeter.

16. A method for fractionating large and small macromolecules according to their respective sizes which comprises the steps of:

providing a device having a substrate with a plurality of individual obstacles extending outwardly therefrom and arranged in a plurality of rows and a plurality of columns to establish a plurality of fluid channels between adjacent columns of said obstacles;

creating a substantially uniform electric field directed substantially parallel to said columns of obstacles to define a forward direction of migration for the macromolecules through said fluid channels of said device, and wherein each said obstacle has a left front wall and a right front wall, said front walls being symmetrical to each other and respectively inclined to redirect macromolecules diffused from one said fluid channel back into said same fluid channel during migration of the macromolecules through said device; and periodically reversing said electric field to cause a reverse migration of the macromolecules through said device in a reverse direction the magnitude of said electric field being greater in the reverse direction than in the forward direction to allow more time for said faster diffusing small macromolecules to leave said channel and separate from said large macromolecules, said reverse direction being substantially opposite said forward direction.

17. A method as recited in claim 16 wherein each said obstacle further includes a left rear wall and a right rear wall, said rear walls being symmetrical to each other and respectively inclined to redirect macromolecules diffused from one said fluid channel back into said same fluid channel during said reverse migration of the macromolecules through said device.

* * * * *

UNITED STATES PATENT AND TRADEMARK OFFICE
CERTIFICATE OF CORRECTION

PATENT NO. : 6,027,623
DATED : February 22, 2000
INVENTOR(S) : Tihiro Ohkawa

It is certified that error appears in the above-identified patent and that said Letters Patent is hereby corrected as shown below:

Title page, item [54], and col. 1, line 2, delete "FRACTION" and insert -- FRACTIONATION--

Signed and Sealed this

Fourteenth Day of November, 2000

Attest:

Q. TODD DICKINSON

Attesting Officer     Director of Patents and Trademarks